(12) United States Patent
Sogaro (10) Patent No.: US 9,694,148 B2
(45) Date of Patent: Jul. 4, 2017

(54) DISCHARGE DEVICE FOR A FLOWABLE SUBSTANCE

(75) Inventor: Alberto C. Sogaro, Frankfurt (DE)

(73) Assignee: DISPENSYS AG, Basel (CH)

( * ) Notice: Subject to any disclaimer, the term of this patent is extended or adjusted under 35 U.S.C. 154(b) by 755 days.

(21) Appl. No.: 13/982,906

(22) PCT Filed: Jan. 26, 2012

(86) PCT No.: PCT/EP2012/051244
§ 371 (c)(1),
(2), (4) Date: Nov. 20, 2013

(87) PCT Pub. No.: WO2012/104199
PCT Pub. Date: Aug. 9, 2012

(65) Prior Publication Data
US 2014/0060523 A1 Mar. 6, 2014

(30) Foreign Application Priority Data

Feb. 2, 2011 (EP) .................................. 11153081

(51) Int. Cl.
*A61M 11/02* (2006.01)
*A61M 15/08* (2006.01)
(Continued)

(52) U.S. Cl.
CPC ........... *A61M 11/02* (2013.01); *A61M 11/007* (2014.02); *A61M 15/08* (2013.01); *B05B 1/34* (2013.01); *B05B 11/02* (2013.01)

(58) Field of Classification Search
CPC .. A61M 11/00; A61M 11/001; A61M 11/002; A61M 11/006; A61M 11/007;
(Continued)

(56) References Cited

U.S. PATENT DOCUMENTS

| 4,034,900 A | * | 7/1977 | Hafele | F04B 7/04 |
| | | | | 222/321.9 |
| 4,842,495 A | * | 6/1989 | Howlett | B05B 11/0059 |
| | | | | 222/321.4 |

(Continued)

FOREIGN PATENT DOCUMENTS

| DE | 200 19 091 U1 | 4/2001 |
| EP | 1 504 783 A1 | 2/2005 |

(Continued)

OTHER PUBLICATIONS

PCT English Translation of the International Preliminary Report on Patentability, PCT/EP2012/051244, Aug. 15, 2013, 11 pages.

(Continued)

*Primary Examiner* — (Jackie) Tan-Uyen T Ho
*Assistant Examiner* — Joseph D Boecker
(74) *Attorney, Agent, or Firm* — Quarles & Brady LLP (57) ABSTRACT

A discharge device for a flowable substance includes at least one storage element having at least one reception chamber for a flowable substance. A carrier body including a discharge opening is provided with a pin having an axial channel and a transverse channel branching off from the axial channel. The storage element is guided on an outer side of the carrier body via at least one annular sealing lip. Discharge of the flowable substance is effected by sliding the storage element onto the pin so that the sealing lip skims over the transverse channel of the cylindrical pin and the cylindrical pin urges the flowable substance out of the reception chamber via the transverse and axial channels. In the area of the discharge opening, the carrier body includes an atomizing device that discharges the flowable substance in atomized form by a sliding of the storage element.

17 Claims, 11 Drawing Sheets

(51) Int. Cl.
  *B05B 1/34* (2006.01)
  *B05B 11/02* (2006.01)
  *A61M 11/00* (2006.01)

(58) Field of Classification Search
  CPC .. A61M 11/02; A61M 15/00; A61M 15/0003; A61M 15/08; A61M 2202/30; A61M 5/19; A61M 5/315; A61M 5/3153; A61M 5/31596; B05B 1/005; B05B 1/02; B05B 1/26; B05B 1/262; B05B 1/265; B05B 1/34; B05B 11/00; B05B 11/0008; B05B 11/0078; B05B 11/0081; B05B 11/0089; B05B 11/0091; B05B 11/3004; B05B 11/3015; B05B 11/3043; B05B 11/3081; B05B 11/3084; B05B 11/3085
  USPC ............ 128/200.14, 200.18, 200.19, 203.22, 128/203.23; 604/194–196, 221, 231, 236, 604/238; 239/329, 469, 474, 538, 539, 239/541, 601; 222/321.6, 320, 321.2
  See application file for complete search history.

(56) References Cited

U.S. PATENT DOCUMENTS

| | | | | |
|---|---|---|---|---|
| 5,046,644 A | * | 9/1991 | Cater | B05B 11/3019 222/321.2 |
| 5,224,471 A | * | 7/1993 | Marelli | B05B 11/0005 128/200.14 |
| 5,289,818 A | * | 3/1994 | Citterio | B05B 11/02 128/200.14 |
| 5,348,189 A | * | 9/1994 | Cater | B05B 7/0031 222/1 |
| 5,692,649 A | * | 12/1997 | Schwab | B05B 11/004 141/65 |
| 5,819,730 A | * | 10/1998 | Stone | A61M 15/0028 128/200.14 |
| 6,234,365 B1 | * | 5/2001 | Bougamont | A61M 11/06 222/189.06 |
| 6,447,476 B1 | * | 9/2002 | Sogaro | A61C 5/064 604/85 |
| 7,367,478 B2 | * | 5/2008 | Fuchs | B05B 11/3035 222/321.6 |
| 7,963,937 B2 | * | 6/2011 | Pauser | A61C 9/0026 222/129 |
| 2002/0003150 A1 | * | 1/2002 | Hermouet | B05B 11/3023 222/321.2 |
| 2002/0087122 A1 | * | 7/2002 | Sogaro | A61M 5/19 604/191 |
| 2002/0195100 A1 | * | 12/2002 | Webb | A61M 11/06 128/200.14 |
| 2006/0261092 A1 | * | 11/2006 | Ophardt | B05B 11/3067 222/181.1 |
| 2008/0230633 A1 | * | 9/2008 | Harms | A61M 15/08 239/463 |
| 2009/0013994 A1 | * | 1/2009 | Jones | A61M 11/008 128/200.23 |
| 2009/0188948 A1 | * | 7/2009 | Stern | B05B 1/02 222/402.1 |
| 2010/0095957 A1 | | 4/2010 | Corbacho | |
| 2011/0057055 A1 | * | 3/2011 | Wong | B05B 11/02 239/329 |
| 2013/0298902 A1 | * | 11/2013 | Denton | A61M 11/06 128/200.14 |

FOREIGN PATENT DOCUMENTS

| | | | | |
|---|---|---|---|---|
| EP | 2 011 467 A1 | | 1/2009 | |
| GB | 2 403 153 A | | 12/2004 | |
| GB | 2403153 A | * | 12/2004 | ........ A61M 15/0028 |

OTHER PUBLICATIONS

International Search Report and Written Opinion under date of mailing of Mar. 4, 2012 in connection with PCT/EP2012/051244.

* cited by examiner

DISCHARGE DEVICE FOR A FLOWABLE SUBSTANCE

CROSS-REFERENCE TO RELATED APPLICATIONS

This application represents the national stage entry of PCT International Application No. PCT/EP2012/051244 filed on Jan. 26, 2012, which claims the benefit of European Patent Application 11153081.2 filed on Feb. 2, 2011. The disclosure of each of these applications is hereby incorporated by reference.

The invention relates to a discharge device for a flowable substance, in particular for a drug and/or a vaccine, having the features of the preamble of patent claim 1.

Discharge devices of this kind are known, for example, from DE 200 19 091 U1 and serve in particular to administer pharmaceutical or cosmetic substances to the human body. The known administering device is formed in the manner of a mini syringe and comprises a carrier body, which is provided with a discharge opening for the discharge of the flowable substance at the front side. On the side facing away from the discharge opening, the carrier body has a cylindrical pin, which has an axial channel and a transverse channel branching off from the axial channel. At the cylindrical pin, meaning on its outer side, a storage element is guided via two axially spaced sealing lips. The storage element is formed pot-shaped or in the form of a small tube closed on one side and can be slid manually on the cylindrical pin in such a manner that the pin acts as a displacement piston which displaces the flowable substance stored in the storage element and transports it via the transverse channel and the axial channel of the carrier body to the discharge opening.

By means of the discharge device known from DE 200 19 091 U1, the flowable substance may not be dischargeable in a sufficiently atomized manner.

It is the task of the invention to create an administering device according to the aforementioned type, which in contrast to the state of the art is characterized by improved atomizing properties.

This task is solved according to the invention by the discharge device having the features of patent claim 1.

According to the invention, in the area of the discharge opening, the carrier body thus comprises an atomizing device, via which the flowable substance is discharged in atomized form by means of a sliding of the storage element.

The discharge device of the invention can be employed in particular to administer a drug or a vaccine into a nostril of a human or also to apply a drug or a vaccine to the pharyngeal mucosa of a human. In general, the discharge device according to the invention is suitable for single- or multi-component systems, which are to be subjected to an atomization or nebulization when administered.

In a preferred embodiment of the discharge device according to the invention, the atomizing device comprises a nozzle, which is arranged downstream of an atomizing chamber, in which a deflecting element is arranged so that a flowable substance is discharged in atomized form via the nozzle. In this context, the deflecting element acts as a guiding device in such a manner that the flowable substance is transported to the nozzle in a radially outward offset manner with regard to the axis of the nozzle. This means that in the atomizing chamber, the flowable substance is transported eccentrically to the nozzle, which improves the atomizing properties of the discharge device.

In a special embodiment of the discharge device according to the invention, the deflecting element is formed from a small plate-shaped or ball-shaped element, at the circumference of which the flowable substance is transported in the direction of the nozzle. The circumference of deflecting element formed in that manner, together with the wall of the atomizing chamber, defines the flow path of the flowable substance.

In the discharge device according to the invention, a discharge channel, which is engaged by a reduction rod, can be arranged upstream of the atomizing chamber to further optimize the atomizing behavior. Together with the wall of the discharge channel, the reduction rod forms an annular channel, through which the flowable substance is transported to the atomizing chamber. The reduction rod also serves the purpose of leaving as little residue as possible in the discharge device after the use of the discharge device. This means the reduction rod limits the volume of the discharge channel.

To make sure that assembling the discharge device according to the invention is simple, the reduction rod can be formed integrally with the deflecting element.

In an embodiment that can be cost-effectively realized in terms of production, the cylindrical pin is formed by an insert, which is locked to the carrier body in particular via an annular shoulder.

The insert forming the cylindrical pin is preferably inserted from one side into the carrier body. From the side facing away from the insert, the reduction rod provided with the deflecting element is then advantageously inserted through the discharge opening and the discharge channel so that the deflecting element is arranged within the atomizing chamber. For fixing the reduction rod, a pot-shaped nozzle insert can be used, which radially delimits the atomizing chamber and on the front side of which the nozzle is formed.

In particular in a discharge device that is configured for a single-component system and comprises a reception chamber for a flowable substance and a cylindrical pin and in which the axial channel of the pin is aligned with the discharge channel adjoining the atomizing chamber, the reduction rod can engage the axial channel of the pin and preferably penetrate the latter to a large extent.

Furthermore, for fixing the insert, the carrier body can have an axial passage, which is formed in a stepped manner and which is engaged by the insert. The discharge channel can be part of the passage or merge into the latter.

In a discharge device for a multi-component system or for a flowable substance which is stored in multiple storage chambers of the storage element, at least two of the pins can be formed on the insert, at each of which one storage element is slidably guided or at which a single storage element with a corresponding number of reception chambers is slidably guided. In any case, one pin, respectively, engages one reception chamber. Also, multiple inserts with one pin, respectively, can be provided.

Between the insert with multiple pins and the carrier body, a guiding piece can be arranged, which at least in part forms the discharge channel leading to the atomizing chamber. In the guiding piece, which is also inserted into the carrier body, a mixing of the components can take place in a multi-component system. From the guiding piece, the substance to be discharged is guided, where applicable in mixed form, to the discharge channel.

To facilitate the administration of the flowable substance, preferably, at least one finger rest surface is formed on the carrier body or the storage element comprises a plunger surface, which can be formed on a plunger plate. The discharge device according to the invention can thus be operated in the manner of a customary disposable syringe so that when it is used, two fingers of a user come to rest on the finger rest surfaces of the carrier body and the user's thumb pushes against the plunger surface of the storage element so that the discharge device is telescoped, i.e. compressed, and the cylindrical pin or pins discharges or discharge the flowable substance from the reception chamber or chambers in the manner of a displacement piston.

In order to be able to dose the drug, which is received by the discharge device of the invention or by the reception chamber of the storage element, in a defined manner in multiple steps, in a special embodiment of the discharge device according to the invention, at least one detachable stop element is provided, which delimits a relative motion between the storage element and the carrier body. When being administered, in a first stage, the drug or vaccine can thus first be discharged from the discharge device until the stop element is reached. For a second administration stage, the stop element is detached so that a further relative motion between the storage element and the carrier body is possible. This embodiment is particularly suitable for the case in which a vaccine is to be administered in equal amounts into both nostrils of a human nose.

Further advantages and advantageous embodiments of the subject matter of the invention can be taken from the description, the drawing and the patent claims.

Four exemplary embodiments of a discharge device according to the invention are illustrated in a schematically simplified manner in the drawing and will be explained in more detail in the following description.

In FIGS. 1 to 8, a discharge device 10 is illustrated, which is formed in the manner of a syringe and serves to administer a liquid drug or a vaccine into the human nose.

Figure 3:
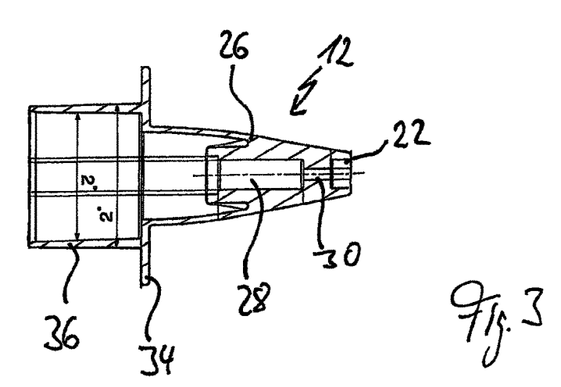
FIG. 3 shows a longitudinal section through a carrier body of the discharge device in individual display.
Figure 4:
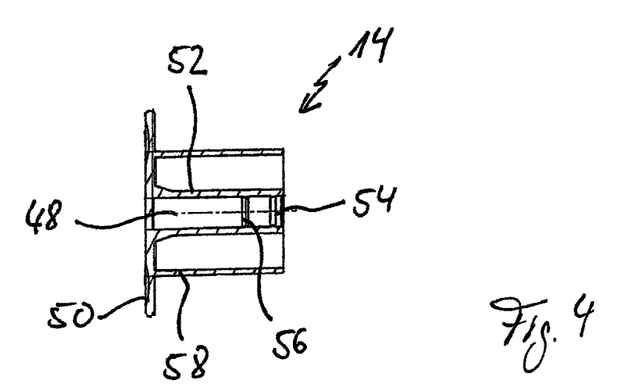
FIG. 4 shows a longitudinal section through a storage element of the discharge device in individual display.
Figure 5:
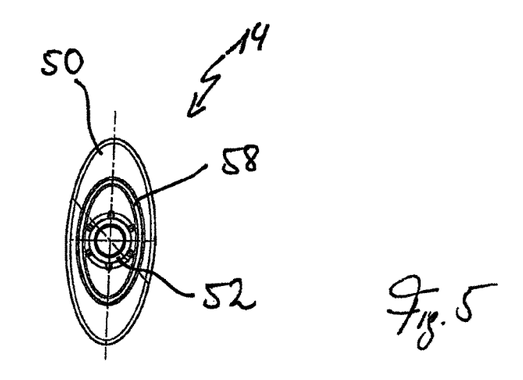
FIG. 5 shows a frontal view of the storage element.

The discharge device 10 comprises a carrier body or syringe body 12, which is illustrated in individual display in FIG. 3, and a storage element 14, which is formed as a plunger and which is illustrated in FIGS. 4 and 5 in individual display. As further components, the discharge device 10 comprises a rod-shaped or substantially cylindrical insert 16, a reduction rod 60 and a nozzle insert 20, which, in the area of a discharge opening 22 of the carrier body 12, comprises a nozzle 21 for discharging the drug 24 stored in the storage element 14.

The carrier body 12 comprises a socket 26, which has a largely elliptical cross section tapering in the direction of the discharge opening 22, and which is interrupted in the axial direction by a passage 28 formed in a stepped manner. The passage 28 has a discharge channel 30, which ends in an atomizing chamber 32. In the atomizing chamber 32, in the assembled state, the nozzle insert 20 formed pot-shaped is fixed so that its circumferential wall radially delimits the atomizing chamber 32.

On the side facing away from the atomizing chamber 32, the socket 26 is delimited by a finger rest plate 34, the plane of which is oriented at a right angle to the axis of the carrier body 12. The finger rest plate 34 is adjoined by a guiding wall 36, which extends in the axial direction of the carrier body 12 and also has a substantially elliptical form with a constant diameter.

Figure 1:
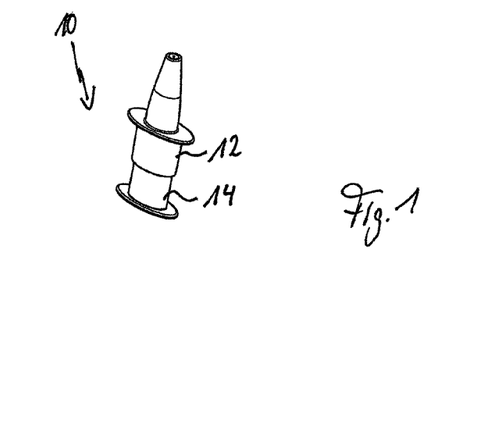
FIG. 1 shows a perspective view of a discharge device comprising a reception chamber for a flowable substance.
Figure 2:
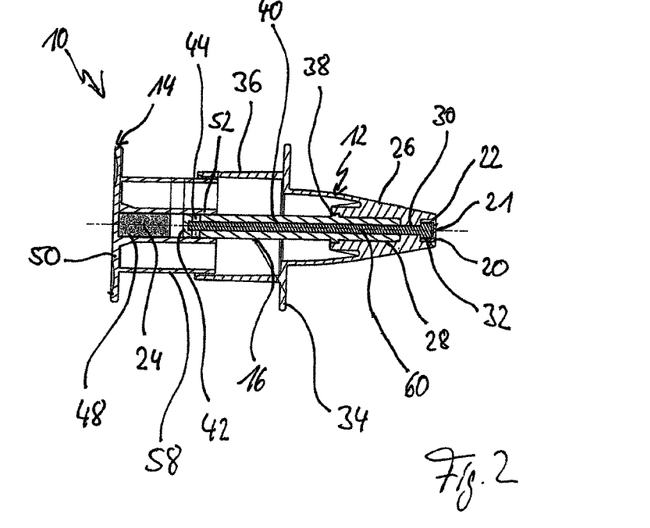
FIG. 2 shows a longitudinal section through the discharge device of FIG. 1.

Into the passage 28 of the socket 26, from the side facing away from the nozzle insert 20, the cylindrical insert 16 is inserted and locked by means of an annular shoulder 38, which corresponds to the steps of the passage 28.

Figure 6:
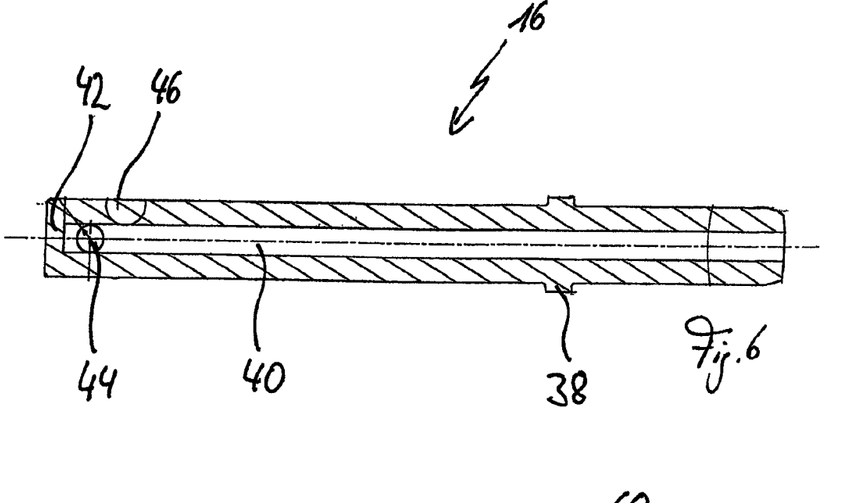
FIG. 6 shows a longitudinal section through an insert of the carrier body.

The insert 16, which is formed in the manner of a tube with an end closed at one side, has an axial channel 40, as can be taken in particular from FIG. 6, which extends from the front side facing the atomizing chamber 32 to a front wall 42 and from which, in the end portion adjoining the front wall 42, a transverse channel 44 branches off, which penetrates the wall of the insert 16. Further, on the circumference of the insert 16 with regard to the transverse channel 44 offset in the direction of the atomizing chamber 32, an annular lip 46 is arranged, at which the storage element 14 formed as a plunger is guided.

As described in the above, the storage element 14 is formed as a plunger so that by its actuation the liquid drug 24, which is stored in a reception chamber 48 of the storage element 14, can be discharged from the discharge device 10.

At the front side, on the one hand, the reception chamber 48 is delimited by a plunger plate 50 of the storage element 14 and in the assembled state, on the other hand, it is delimited by the front wall 42 of the insert 16. Radially, the reception chamber 48 is delimited by an inner wall 52, which has a circular outline and on the inner side of which two sealing lips 54 and 56 are arranged, which are spaced from each other in the axial direction of the insert 16 and whose distance is slightly larger than the diameter of the transverse channel 44 of the insert 16. Via the sealing lips 54 and 56 and the lip 46 of the insert 16, the storage element 14 is slidably guided at the insert 16. In this context, the sealing lips 54 and 56 of the storage element 14, on the one hand, and the lip 46 of the insert 16, on the other hand, can act as stops, which can convey the respective operating position of the storage element 14 with regard to the insert 16 to the user. However, the sealing lips 54 and 56 can slide past the lip 46 of the insert 16 when the storage element 14 is actuated.

The storage element 14 further comprises an outer wall 58, which has an elliptical outline and encloses the inner wall 52 and is guided at the inner side of the guiding wall 36 of the carrier body 12 or is slid with little distance to the guide wall 36 when the storage element 14 is actuated.

Figure 7:
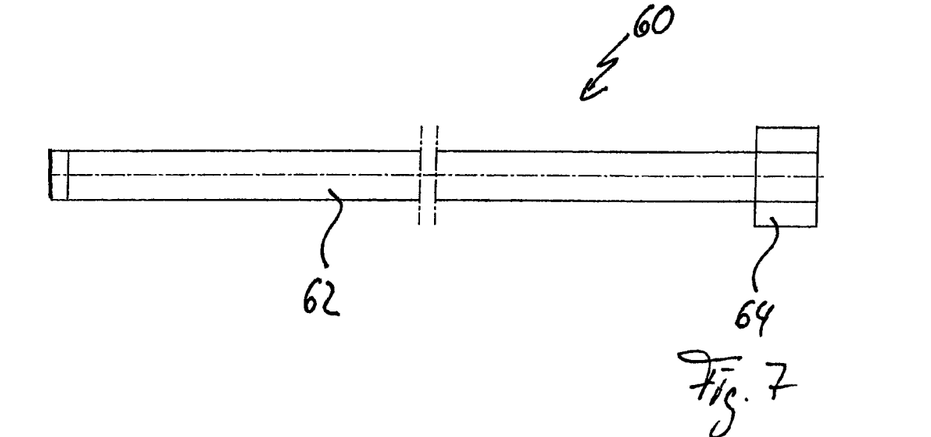
FIG. 7 shows a lateral view of a reduction rod of the discharge device.
Figure 8:
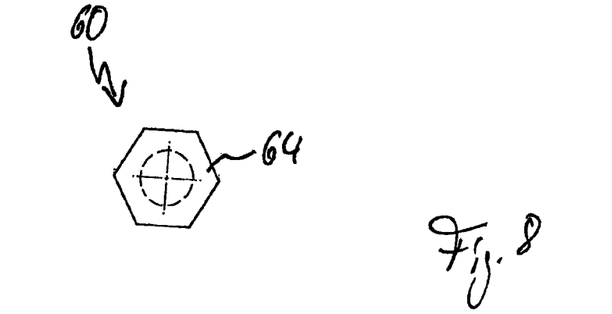
FIG. 8 shows a frontal view of the reduction rod according to arrow VIII in FIG. 7.
Figure 9:
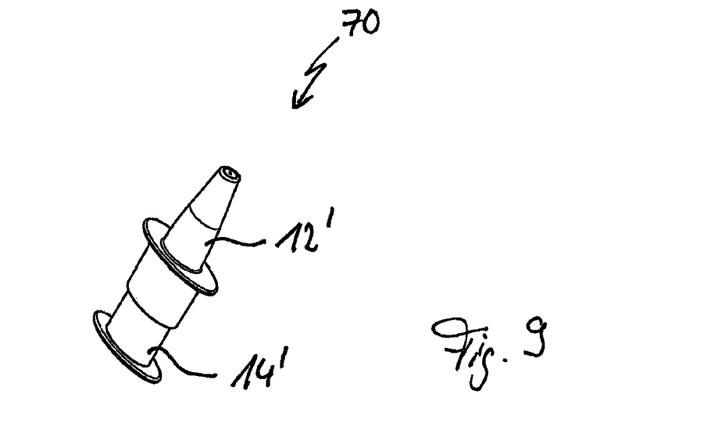
FIG. 9 shows a perspective view of a second embodiment of a discharge device comprising two reception chambers for a flowable substance.
Figure 10:
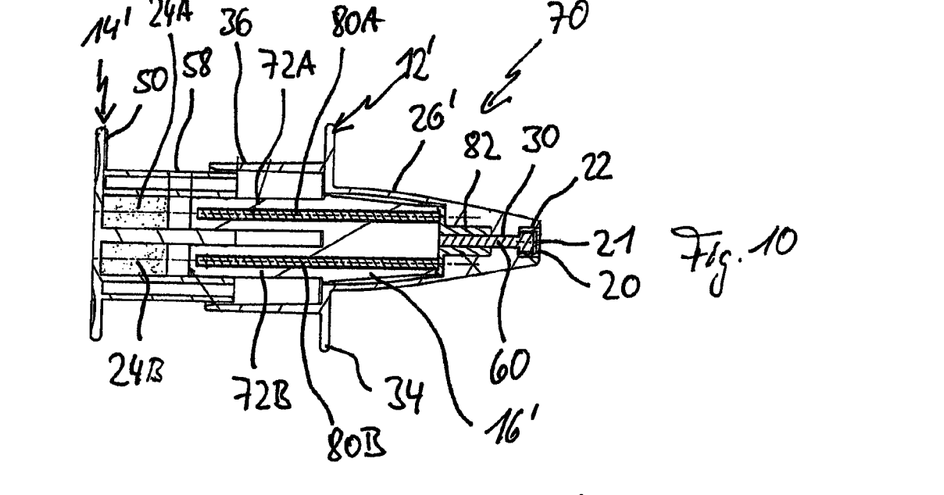
FIG. 10 shows a longitudinal section through the discharge device of FIG. 9.
Figure 11:
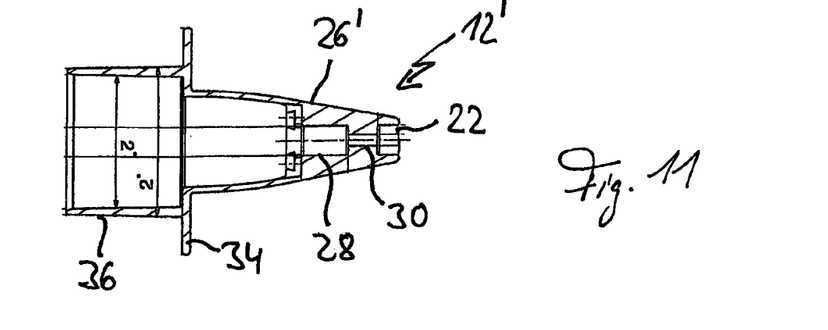
FIG. 11 shows a longitudinal section through a carrier body of the discharge device of FIG. 9.
Figure 12:
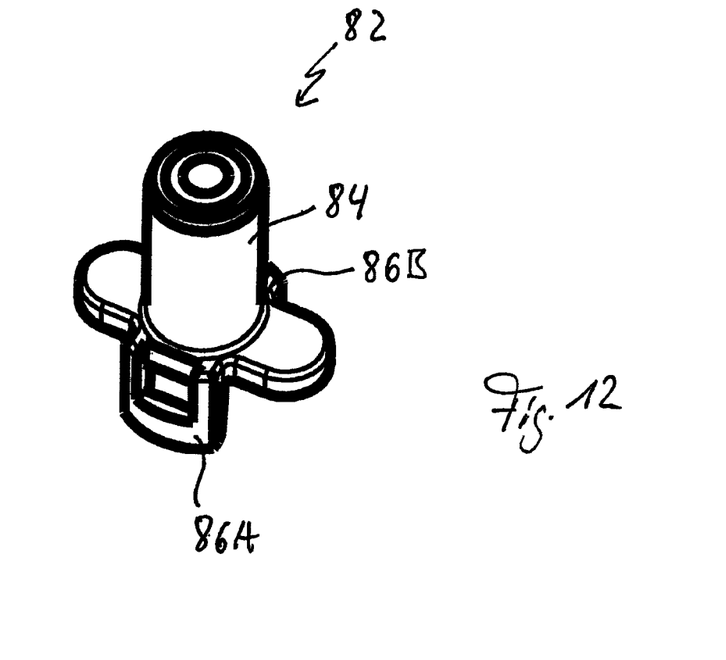
FIG. 12 shows a perspective view of a guiding piece of the discharge device of FIG. 9.
Figure 13:
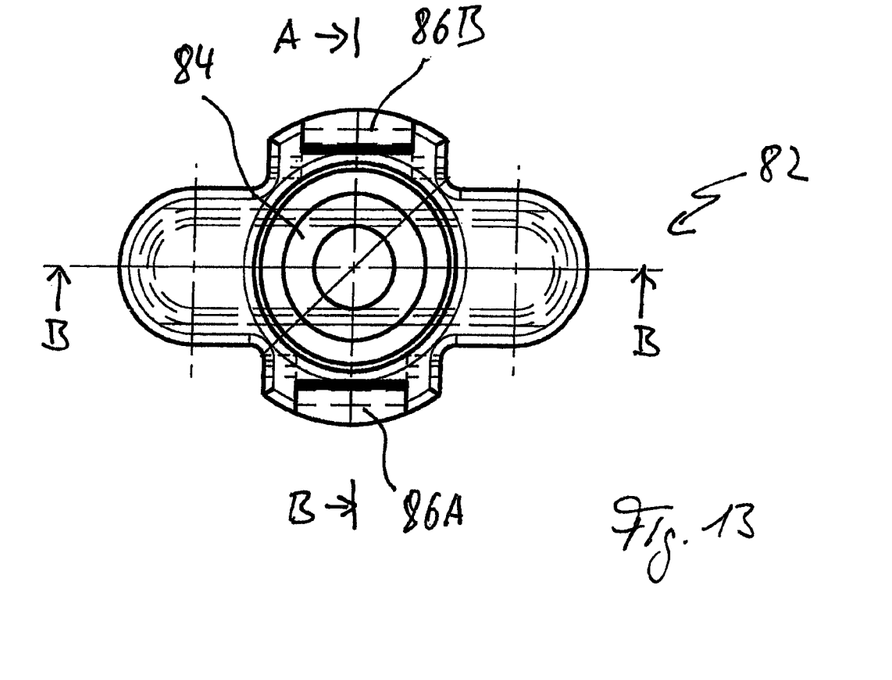
FIG. 13 shows a frontal view of the guiding piece.
Figure 14:
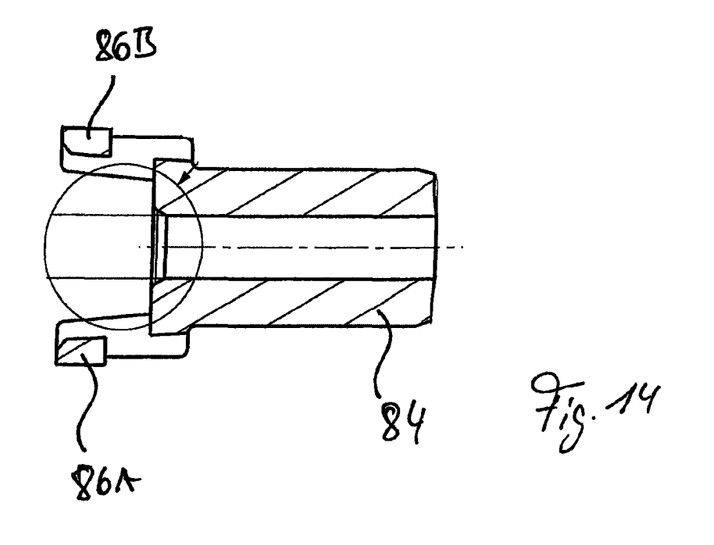
FIG. 14 shows a section through the guiding piece if FIG. 12 along the line A-A in FIG. 13.
Figure 15:
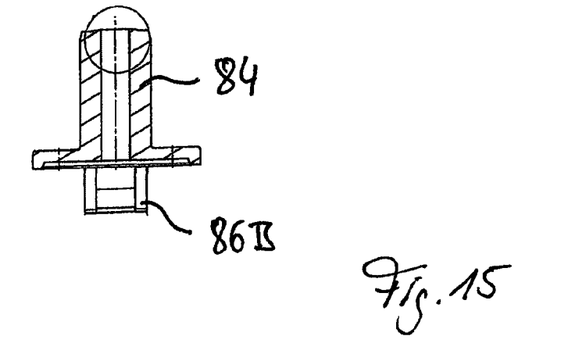
FIG. 15 shows a section along the line B-B in FIG. 13.
Figure 16:
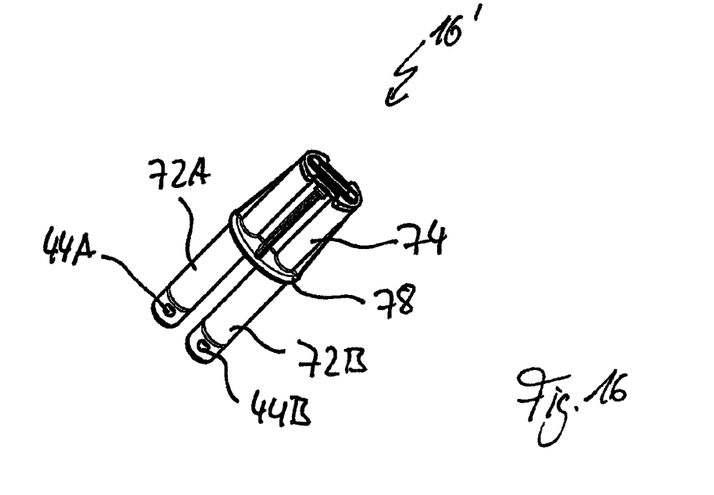
FIG. 16 shows a perspective view of an insert of the discharge device of FIG. 9.
Figure 17:
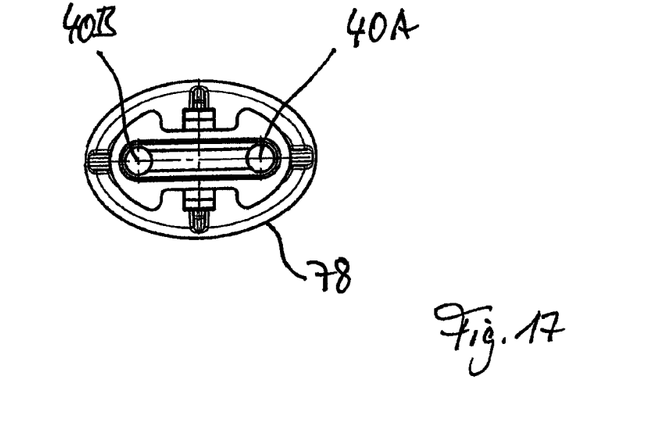
FIG. 17 shows a frontal view of the insert of FIG. 16.
Figure 18:
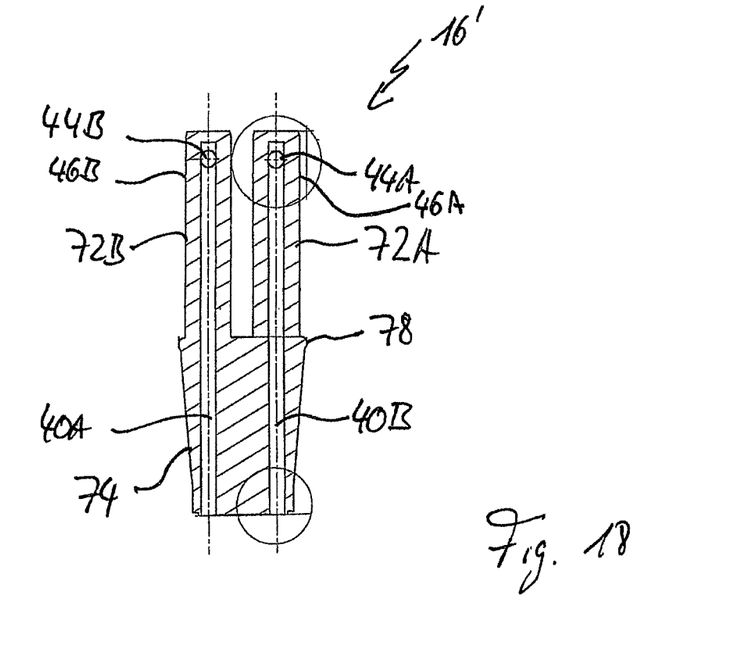
FIG. 18 shows a section through the insert of FIG. 16 along the line A-A in FIG. 17.
Figure 19:
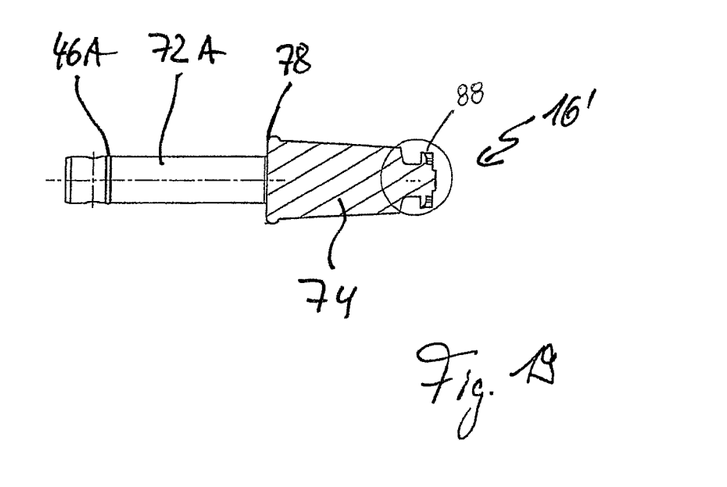
FIG. 19 shows a section through the insert of FIG. 16 along the line B-B in FIG. 17.
Figure 20:
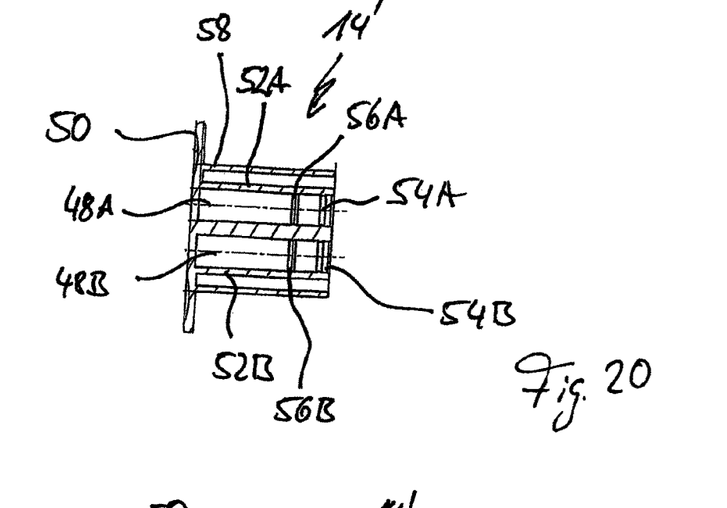
FIG. 20 shows a first section through a storage element of the discharge device of FIG. 9 with two storage chambers.
Figure 21:
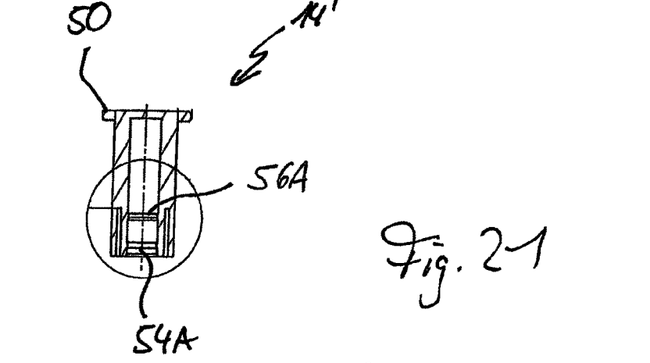
FIG. 21 shows a second section through the storage element of FIG. 20.
Figure 22:
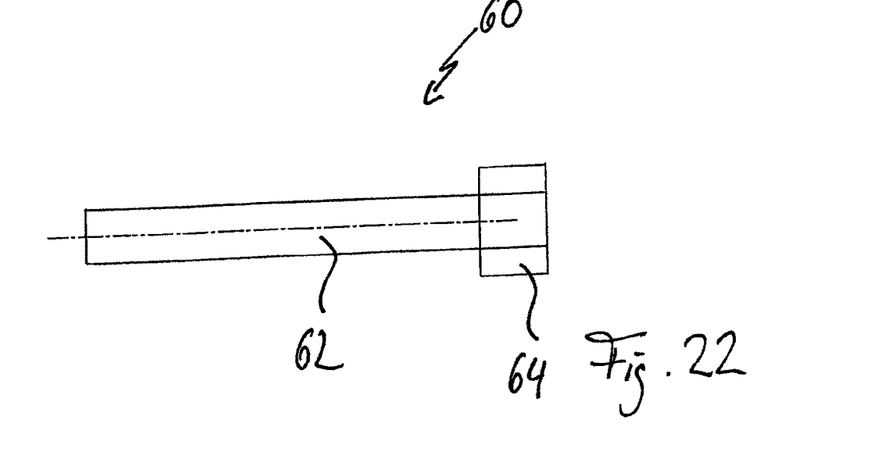
FIG. 22 shows a lateral view of a reduction rod of the discharge device of FIG. 9.
Figure 23:
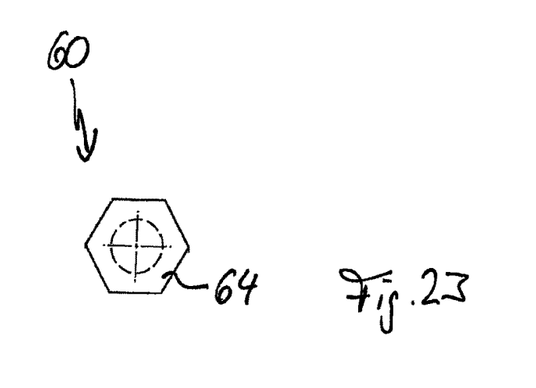
FIG. 23 shows a frontal view of the reduction rod according to arrow X in FIG. 22.

The discharge device 10 further comprises a reduction rod 60, which is illustrated in individual display in FIGS. 7 and 8 and which has a cylindrical shaft 62, which completely penetrates the discharge channel 30 of the carrier body 12 and the axial channel 40 of the insert 16. The diameter of the shaft 62 of the reduction rod 60 is slightly smaller than the diameter of the axial channel 40 of the insert 16 and of the discharge channel 30 of the carrier body 12.

On its end facing away from the insert 16, the reduction rod 60 has a small plate-shaped head 64, which is formed in the manner of a hexagonal prism and which forms a deflecting element for the drug to be discharged from the discharge device. The head 64 is arranged within the atomizing chamber 32 so that, together with the pot-shaped nozzle insert 20, it defines the flow path of the drug in the atomizing chamber 32. On the bottom of the nozzle insert, on the inner side, grooves are formed, through which the drug flows towards the nozzle 21 so as to be atomized or nebulized there.

In the storage position illustrated in FIG. 2, the sealing lips 54 and 56 abut in such a manner against the outer side of the insert 16 forming a pin that the transverse channel 44 is arranged between them. To administer the drug 24 stored in the reception chamber 48, the storage element 14 is slid in the direction of the socket 26 of the carrier body 12 by applying pressure on the front side of the insert 16 so that the sealing lip 56 skims the transverse channel 44 and a fluid communication between the reception chamber 48 and the transverse channel 44 via a ring chamber formed between the inner wall 52 and the circumference of the insert 16 is opened. By a continued pushing or a continued sliding of the storage element 14 on the insert 16, the drug 24 is then displaced from the reception chamber 48 by the insert 16, transported via the transverse channel 44 and the ring chamber formed by the shaft 62 of the reduction rod 60 and the insert 16, into the axial channel 30 and the ring chamber formed in the area of the discharge channel 30 by the shaft 62 of the reduction rod 60 and the socket 26 of the carrier body 12, towards the atomizing chamber 32, and discharged from there in atomized form via the nozzle 21 by means of the formation of the head 64. By means of the reduction rod 60, the drug 24 can be discharged from the discharge device 10 substantially without any residue.

In FIGS. 9 to 22, a discharge device 70 is illustrated, whose outer appearance corresponds to that of the discharge device according to FIGS. 1 to 8. However, the discharge device 70 is suitable for the administration of a drug composed of two components 24A and 24B. For this purpose, the discharge device 70 comprises a storage element 14', which is formed as a plunger and has two reception chambers 48A and 48B for one drug component 24A or 24B, respectively, which each are delimited by a circular inner wall 52A or 52B, respectively. According to the embodiment of FIGS. 1 to 8, the storage element 14' also comprises an outer wall 58, which has a substantially elliptic outline.

The two inner walls 52A and 52B of the storage element 14' each comprise two sealing lips 54A and 56A or 54B and 56B, respectively, which serve to guide the storage element 14' at two cylindrical pins 72A and 72B of an insert 16', which is fixed in a carrier body 12' of the discharge device 70. As it can be taken from FIGS. 16 to 19, the insert 16' has a socket 74, which serves as a locking portion and which is locked in a recess 76 of a socket 26' of the carrier body 12'. For this purpose, the socket 74 has a locking shoulder 78.

From the socket 74, the two pins 72A and 72B branch off, at which the storage element 14 is guided and which, corresponding to the insert illustrated in FIG. 6, each have a lip 46A or 46B, respectively, which abuts against the inner side of the respective inner wall 52A or 52B of the storage element 14'.

Further, the two pins 72A and 72B of the insert 16' each comprise an axial channel 40A or 40B, respectively, which, on the side facing the storage element 14, is delimited by a respective front wall 52A or 52B and penetrates the socket 74 as far as to the front side facing away from the storage element 14'. Further, from the axial channels 40A and 40B, one transverse channel 44A or 44B branches off, respectively, whose function corresponds to the function of the transverse channel of the insert according to FIG. 6.

In the axial channels 40A and 40B, one reduction rod 80A or 80B is arranged, respectively, which serves to minimize drug residue when the drug is discharged.

To the front side of the insert 16' facing away from the storage element 14', a guiding piece 82 adjoins, which is illustrated in individual display in FIGS. 12 to 15 and has a tube portion 84 engaging a passage 28 of the carrier body 12' and two foot portions 86A and 86B, which are formed as locking flaps and which can be locked with a corresponding head portion 88 of the insert 16' shown in FIG. 19. In the guiding piece 82, the drug components discharged from the reception chambers 48A and 48B are mixed and subsequently transported through the tube portion 84 towards an atomizing chamber 32, which is formed at the front side in the socket 26 of the carrier body 12' and which is formed corresponding to the atomizing chamber of the embodiment according to FIGS. 1 to 8. Also in accordance with the embodiment of FIGS. 1 to 8, at the socket 26' in the area of a discharge opening 22, a pot-shaped nozzle insert 20 is inserted, which radially delimits the atomizing chamber 32 and forms a nozzle 21.

Further, also the embodiment illustrated in FIGS. 9 to 23 comprises a reduction rod 60, which has a head 64 formed in a hexagonally prismatic manner and a shaft 62, the head 64 being arranged in the atomizing chamber 32 and the shaft 62 being arranged in the discharge channel 30 and the tube portion 84 of the guiding piece 82 and serving to reduce the inner volume of the discharge device 70.

When administering the drug stored in the discharge device 70, the user exerts pressure on the plunger plate 50 of the storage element 14' so that the discharge device 70 is telescoped and the storage element 14' is slid at the pins 72A and 72B of the insert 16' in the direction of the socket 26' of the carrier body 12'. In this process, the sealing lips 56A and 56B skim the transverse channels 44A and 44B of the pins 72A and 72B, the components 24A and 24B thus being transported by the piston effect of the pins 72A and 72B via the transverse channels 44A and 44B and the axial channels 40A and 40B to the guiding piece 82, there being mixed and then discharged through the discharge channel 30 and the atomizing chamber 32 in atomized form via the nozzle 21.

Figure 24:
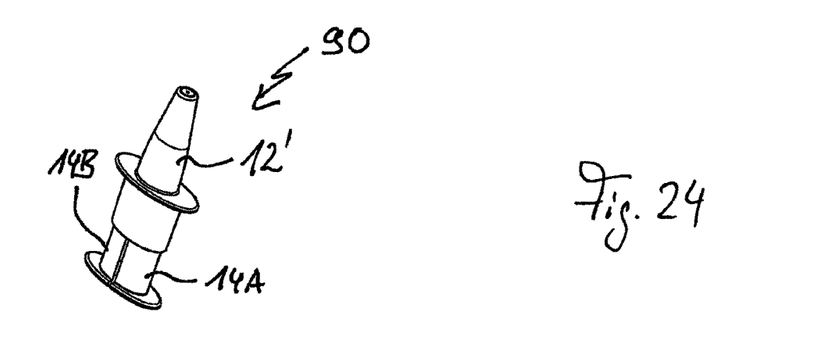
FIG. 24 shows a perspective view of a third embodiment of a discharge device according to the invention.
Figure 25:
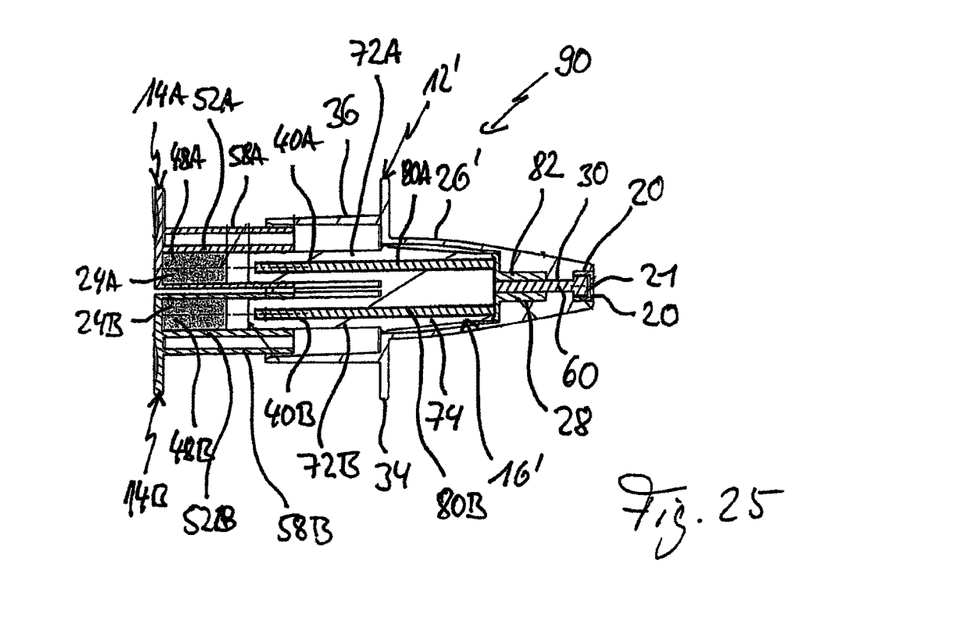
FIG. 25 shows a longitudinal section through the discharge device of FIG. 24.

In FIGS. 24 and 25, another embodiment of a discharge device 90 is illustrated, whose structure substantially corresponds to that of the embodiment according to FIGS. 9 to 23, but differs therefrom in that it comprises two storage elements 14A and 14B, which can be slid separately at the two pins 72A and 72B. For example, the discharge device 90 can be used to administer a first drug component 24A, which is stored in the storage element 14A, into one nostril of a human nose and a second drug component 24B, which is stored in the second storage element 14B, into the second nostril of a human nose.

The storage element 14A, which is associated with pin 72A, comprises a reception chamber 48A for the drug component 42A, and the storage element 14B, which is associated with pin 72B, comprises a reception chamber 48B for the second drug component 24B. Each of the two reception chambers 48A and 48B is delimited by a cylindrical inner wall 52A or 52B, respectively, which is guided at the respectively associated pin 72A or 72B and delimited by an outer wall 58A or 58B, which as a semi-elliptical outline. Correspondingly, the reception chambers 48A and 48B each are delimited at the front side by a plunger plate 50A or 50B, respectively, which has a semi-elliptical base surface.

Otherwise, the structure of the discharge device 90 substantially corresponds to that of the discharge device according to FIGS. 9 to 23.

Figure 26:
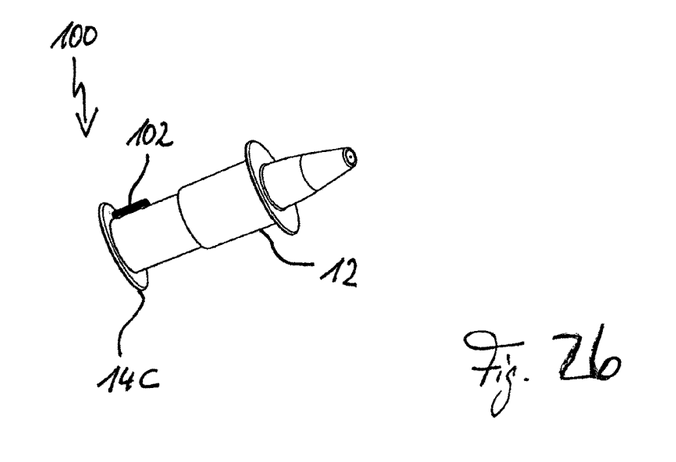
FIG. 26 shows a perspective view of a third embodiment of a discharge device for the two-staged administration of a liquid drug or of a vaccine.
Figure 27:
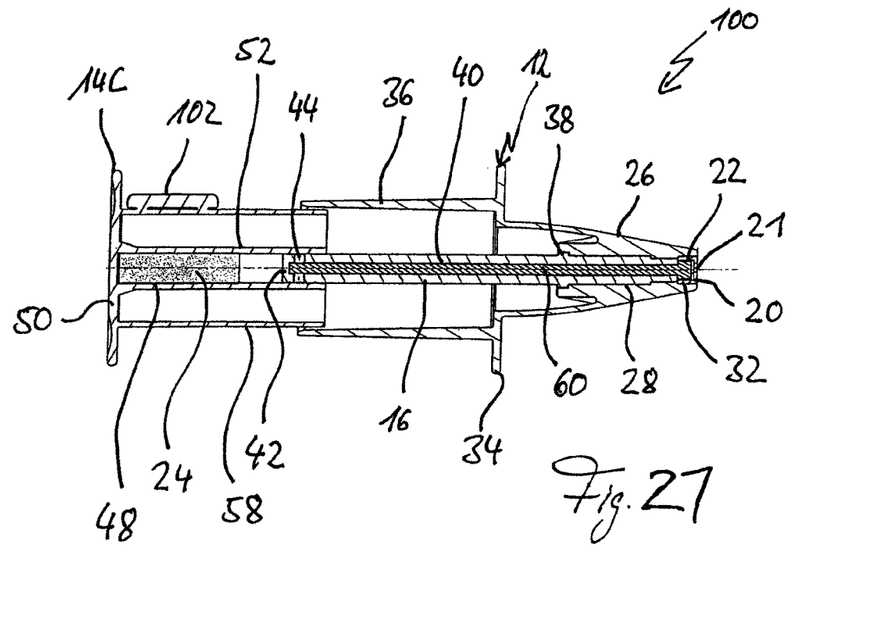
FIG. 27 shows a longitudinal section through the discharge device of FIG. 26.

In FIGS. 26 and 27, a discharge device 100 is illustrated which is also formed like a syringe and serves to administer of a liquid drug or vaccine into the human nose.

The discharge device 100 substantially corresponds to the one illustrated in FIGS. 1 to 8, but differs therefrom in that, on the one hand, the insert 16 completely penetrates the passage 28 of the carrier body 12 and delimits the atomizing chamber 32 at its side facing away from the nozzle 21. On the other hand, at the outer wall 58 of the storage element 14C, a stop element 102 in the form of a flap is integrally formed, which extends in the longitudinal direction or axial direction, respectively, of the discharge device 100 and which delimits the sliding path between the carrier body 12 and the storage element 14C in that it abuts against the guiding wall 36. The stop element 102 is detachable so that the storage element 14C can be slid further with regard to the carrier body 12. Thus, it is possible to administer the drug 24, which is stored in the reception chamber 48 of the storage element 14C, in two stages. In a first stage, the storage element 14C is slid with regard to the carrier body 12 until the stop element 102 abuts against the guiding wall 36. In a second stage, after the stop element 102 has been detached, the storage element 14C is slid further with regard to the carrier body 12 so that the drug 24 remaining in the reception chamber 48 can be discharged.

Otherwise, the discharge device 100 corresponds to the discharge device according to FIGS. 1 to 8.

List of reference signs

| | |
|---|---|
| 10 | Discharge device |
| 12, 12' | Carrier body |
| 14, 14', 14A-14C | Storage element |
| 16, 16' | Insert |
| 20 | Nozzle insert |
| 21 | Nozzle |
| 22 | Discharge opening |
| 24, 24A, 24B | Drug |
| 26, 26' | Socket |
| 28 | Passage |
| 30 | Discharge channel |
| 32 | Atomizing chamber |
| 34 | Finger rest plate |
| 36 | Guiding wall |
| 38 | Annular shoulder |
| 40, 40A, 40B | Axial channel |
| 42 | Front wall |
| 44, 44A, 44B | Transverse channel |
| 46, 46A, 46B | Lip |
| 48, 48A, 58B | Reception chamber |
| 50, 50A, 50B | Plunger plate |
| 52, 52A, 52B | Inner wall |
| 54, 54A, 54B | Sealing lip |
| 56, 56A, 56B | Sealing lip |
| 58, 58A, 58B | Outer wall |
| 60 | Reduction rod |
| 62 | Shaft |
| 64 | Head |
| 70 | Discharge device |
| 72A, 72B | Pin |
| 74 | Socket |
| 76 | Recess |
| 78 | Locking shoulder |
| 80A, 80B | Reduction rod |
| 82 | Guiding piece |
| 84 | Tube portion |
| 86A, 86B | Foot portion |
| 90 | Discharge device |
| 100 | Discharge device |
| 102 | Stop element |

The invention claimed is:

1. A discharge device for a flowable substance, said discharge device comprising:
    at least one storage element having at least one reception chamber for the flowable substance;
    a carrier body slidably coupled to the at least one storage element, and having a discharge opening;
    at least one pin received in the discharge opening, said at least one pin having an axial channel and at least one transverse channel branching off from the axial channel;
    at least one-sealing lip guiding the at least one storage element on an outside of the at least one pin, wherein a discharge of the flowable substance is effected by sliding the at least one storage element onto the at least one pin toward the discharge opening so that the at least one sealing lip skims over the transverse channel of the at least one pin and the at least one pin transports the flowable substance in a manner of a displacement piston out of the reception chamber via the at least one transverse channel and the axial channel towards the discharge opening and the flowable substance is discharged through the discharge opening; and
    an atomizing device in an area of the discharge opening, atomizing the flowable substance discharged through the discharge opening, wherein the atomizing device includes a nozzle arranged downstream of an atomizing chamber, in which a deflecting element is arranged so that the flowable substance is discharged from the nozzle in atomized form, wherein upstream of the atomizing chamber, a discharge channel is arranged, which is engaged by a reduction rod engaging the axial channel of the at least one pin, the reduction rod extending upstream to at least where the at least one transverse channel branches off from the axial channel of the pin.

2. The discharge device according to claim 1, in which the reduction rod is solid.

3. The discharge device according to claim 1, in which together with a wall of the discharge channel, the reduction rod forms an annular channel, through which the flowable substance is transported to the atomizing chamber.

4. The discharge device according to claim 3, in which the reduction rod is formed integrally with the deflecting element.

5. The discharge device according to claim 1 in which the at least one pin is formed by an insert, which is locked to the carrier body via an annular shoulder.

6. The discharge device according to claim 3, in which the axial channel of the at least one pin is aligned with the discharge channel.

7. The discharge device according to claim 2, in which a pot-shaped nozzle insert, which includes the nozzle, radially delimits the atomizing chamber.

8. The discharge device according to claim 5, in which the carrier body has an axial stepped passage into which the insert engages.

9. The discharge device according to claim 5, in which on the insert, at least two pins are formed, at each of which one storage element is slidably guided.

10. The discharge device according to claim 5, in which on the insert, two pins are formed, at which the at least one storage element having two reception chambers is slidably guided with each of the two pins engaging one of the reception chambers.

11. The discharge device according to claim 9, in which each of the two pins has an axial channel and in each of the axial channels, one reduction rod is arranged.

12. The discharge device according to claim 5, in which downstream of the insert, a guiding piece is arranged.

13. The discharge device according to claim 1, in which on the carrier body, at least one finger rest surface is formed.

14. The discharge device according to claim 1, in which the at least one storage element includes a plunger plate.

15. The discharge device according to claim 1, in which at least one detachable stop element is provided, which delimits a relative motion between the storage element and the carrier body.

16. The discharge device according to claim 1, in which at least a portion of said at least one pin is cylindrical, and said at least one sealing lip is annular.

17. The discharge device according to claim 12, in which said guiding piece forms at least in part the discharge channel leading to the atomizing chamber.

* * * * *